United States Patent

Perronnet et al.

[11] 4,039,316
[45] Aug. 2, 1977

[54] 3-METHOXY CROTONANILIDES AS HERBICIDES

[75] Inventors: Jacques Perronnet; Pierre Girault, both of Paris, France

[73] Assignee: Roussel-UCLAF, Paris, France

[21] Appl. No.: 616,416

[22] Filed: Sept. 24, 1975

[30] Foreign Application Priority Data

Oct. 3, 1974 France ............................ 74.33321

[51] Int. Cl.² .................. A01N 9/20; C07C 103/56
[52] U.S. Cl. ............................ 71/118; 71/111; 71/120; 260/453 RW; 260/471 C; 260/553 A; 260/562 R; 260/562 A
[58] Field of Search ................ 260/562 A, 562 R; 71/118

[56] References Cited

U.S. PATENT DOCUMENTS

| | | | |
|---|---|---|---|
| 3,278,597 | 10/1966 | Neighbors | 71/118 |
| 3,852,058 | 12/1974 | Huffman | 260/562 R |
| 3,937,729 | 2/1976 | Teach | 71/118 |

OTHER PUBLICATIONS

Knunyants et al., "Determination of the Bond Strength, etc.," (1958), CA 53, p. 4193 (1959).

*Primary Examiner*—Glennon H. Hollrah
*Attorney, Agent, or Firm*—Hammond & Littell

[57] ABSTRACT

Novel crotonanilides of the formula

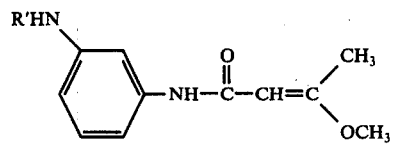

I wherein R' is selected from the group consisting of

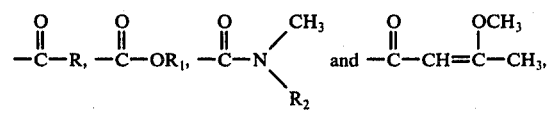

R and $R_1$ are alkyl of 1 to 6 carbon atoms and $R_2$ is selected from the group consisting of hydrogen, methyl and methoxy having pre- and post-emergence herbicidal activity.

11 Claims, No Drawings

3-METHOXY CROTONANILIDES AS HERBICIDES

OBJECTS OF THE INVENTION

It is an object of the invention to provide the novel crotonanilides of formula I as well as a process for their preparation.

It is a further object of the invention to provide novel pre- and post-emergence herbicidal compositions.

It is an additional object of the invention to provide novel methods of killing weeds.

These and other object and advantages of the invention will become obvious from the following detailed description.

THE INVENTION

The novel crotonanilides of the invention have the formula

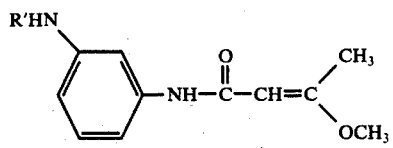

wherein R' is selected from the group consisting of

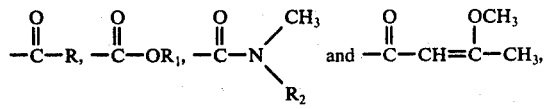

R and $R_1$ are alkyl of 1 to 6 carbon atoms and $R_2$ is selected from the group consisting of hydrogen, methyl and methoxy, R and $R_1$ are preferably methyl, ethyl or linear or branched propyl, butyl, pentyl or hexyl and $R_2$ is preferably methyl or methoxy.

The novel process of the invention for the preparation of the compounds of formula I wherein R' is other than

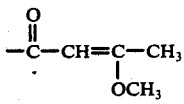

comprises reacting m-nitro-3-methoxy-crotonanilide with a reducing agent to form m-amino-3-methoxy-crotonanilide and condensing the latter with a chloride of the formula R—Cl wherein R' is other than

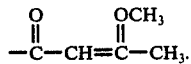

The reducing agent is preferably iron or tin in an acid media and the reduction is preferably effected in the presence of water and in the presence of an organic solvent such as an alkanol. The condensation with the chloride is preferably effected in the presence of a tertiary base such as pyridine or triethylamine and in an organic solvent such as benzene, toluene, tetrahydrofuran, ether or isopropyl ether. The m-nitro-3-methoxy-crotonanilide is described in Belgium Pat. No. 805,281.

Another process of the invention to produce a compound of formula I wherein R' is other than

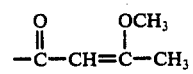

comprises reacting diketene with a compound of the formula

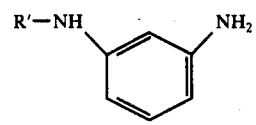

wherein R' has the above definition to obtain a compound of the formula

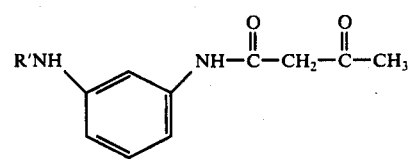

reacting the latter with methyl orthoformate to obtain a compound of the formula

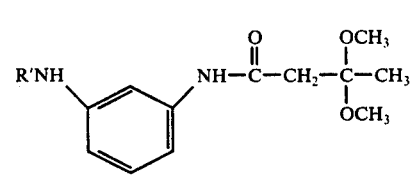

heating the latter to form the corresponding 3-methoxy-crotonanilide.

The reaction with diketene is preferably effected in an organic solvent such as benzene or toluene and the reaction with methyl orthoformate is effected in the presence of an acid agent such as p-toluene sulfonic acid or sulfuric acid. The thermal decomposition is preferably effected in a neutral media in an organic solvent such as toluene or xylene. The preferred heating temperature is about 140° C although lower or higher temperatures may be used.

m-amino-acetanilide is described in Beilstein, Vol. 13, p. 45 and m-aminopropionanilide is described in German Pat. No. 2,124,037 by reduction of the corresponding nitro derivative. m-aminovaleranilide may be made in a similar manner even though it is not described in the literature. Other compounds of formula II may be made in the same manner by reduction of the nitro derivatives obtained by reaction of R'—Cl with nitraniline.

The process of the invention for the preparation of compounds of formula I wherein R' is

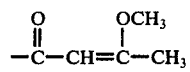

comprises reacting diketene with m-phenylenediamine to obtain m-(acetylacetamido)-acetylacetanilide which is reacted with methyl orthoformate and then heated to obtain m-(3'-methoxycrotonylamino)-3 -methoxy-crotonanilide.

The reactions with diketene and methyl orthoformate are effected as before.

The process of the invention wherein R' is

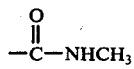

comprises reacting m-amino-3-methoxy-crotonanilide with methyl isocyanate to obtain m-(N-methylureido)-3-methoxy-crotonanilide. The reaction is preferably effected in an organic solvent such as benzene, toluene, tetrahydrofuran, ether or isopropyl ether.

The compounds of formula I may exist in the form of their E isomers or their Z isomers or mixtures thereof. The above processes produces mainly the E isomers.

The novel herbicidal compositions are comprised of a herbicidally effective amount of at least one compound of formula I and a carrier. The compositions are active against a wide variety of botanical families and will selectively destroy weeds without attacking grass crops such as cereals.

The compositions may contain also one or more other pesticidal agents or one or more other products which influence plant growth. The compositions usually contain 10 to 80% by weight, preferably 10 to 50% by weight, of the compounds of formula I.

The compositions may be in the form of powders, granules, suspensions, emulsions or solutions containing besides compounds of formula I; cationic, anionic or non-ionic surface active agents, inert powders such as talc, clays, silicates or kieselguhr, or a vehicle such as water, alcohol, hydrocarbons, other organic solvents or a mineral, vegetable or animal oil.

The novel process of the invention for killing weeds comprises contacting the weeds with a herbicidally effective amount of at least one compound of formula I. The compounds may be applied either per- or post-emergence at a rate of 0.312 to 5 kg/ha.

In the following examples there are described several preferred embodiments to illustrate the invention. However, it is to be understood that the invention is not intended to be limited to the specific embodiments.

EXAMPLE 1 m-(n-propyloxycarbonylamino)-3-methoxy-crotonanilide

STEP A: m-nitro-3-methoxy-crotonanilide

A mixture of 33 g of m-nitro-acetylacetanilide, 38.1 g of methyl orthoformate and 13 drops of 36° Be sulfuric acid was allowed to stand for 16 hours and after the addition of 40 drops of quinoline and 150 ml of toluene, the mixture was heated to 130° C while distilling of the methanol formed as an azeotrope. The mixture was cooled and vacuum filtered and the recovered precipitate was crystallized from acetone to obtain 24 g of m-nitro-3-methoxy-crotonanilide melting at 187° C.

Analysis: $C_{11}H_{12}N_2O_4$. Calculated: %C, 55.92; %H, 5.12; %N, 11.86. Found: %C, 56.1; %H, 5.2; %N, 11.7.

STEP B: m-amino-3-methoxy-crotonanilide 48 g of powdered iron were added over 15 minutes at 20° C to a mixture of 18.9 g of m-nitro-3-methoxy-crotonanilide, 64 ml of 95% ethanol, 16 ml of water and 0.8 ml of 22° Be hydrochloric acid and the mixture was stirred for 1½ hours at 27° C. The interior temperature was raised to 60° C and the temperature was slowly lowered to 25° C. The mixture was filtered and the filtrate was evaporated to dryness under reduced pressure to obtain 13.6 g of m-amino-3-methoxy-crotonanilide. The product melted at 132° C and after crystallization from ethanol still melted at 132° C.

STEP C: m-(n-propyloxycarbonylamino)-3-methoxy-crotonanilide 27 g of propyl chloroformate were slowly added to a mixture of 41.2 g of m-amino-3-methoxy-crotonanilide, 300 ml of tetrahydrofuran and 22.2 g of triethylamine and the mixture was stirred for 16 hours at 20° C. The mixture was filtered and the filtrate was evaporated to dryness under reduced pressure. The residue was chromatographed over silica gel and was eluted with an 8-2 methylene chloride-acetone mixture to obtain 40 g of m-(n-propyloxycarbonylamino)-3-methoxy-crotonanilide melting at 115° C. Crystallization from chloroform did not change the melting point.

Analysis: $C_{15}H_{20}N_2O_7$. Calculated: %C, 61.62; %H, 6.89; %N, 9.58. Found: %C, 61.3; %H, 6.9; %N, 9.3.

EXAMPLE 2 m-(n-butoxycarbonylamino)-3-methoxy-crotonanilide 12 g of n-butyl chloroformate were slowly added to a mixture of 16.5 g of m-amino-3-methoxy-crotonanilide, 320 ml of tetrahydrofuran and 8.9 g of triethylamine cooled to 5° C and the mixture was stirred for 16 hours and then vacuum filtered. The residue was chromatographed over silica gel and was eluted with an 8-2 methylene chloride-acetone mixture to obtain 22 g of m-(n-butoxycarbonylamino)-3-methoxy-crotonanilide melting at 100° C.

Analysis: $C_{16}H_{22}N_2O_4$. Calculated: %C, 62.72; %H, 7.23; %N, 9.14. Found: %C, 62.1; %H, 7.4; %N, 8.7.

EXAMPLE 3 m-(N,N-dimethylureido)-3-methoxy-crotonanilide 32.2 g of dimethylcarbamoyl chloride were added to a mixture of 51.5 g of m-amino-3-methoxy-crotonanilide, 500 ml of tetrahydrofuran and 30 g of triethylamine and the resulting mixture was refluxed for 16 hours and then was concentrated to dryness under reduced pressure. The residue was chromatographed over silica gel and was eluted with an 8-2 methylene chloride-acetone mixture. The product was again subjected to chromatography over silica gel and was eluted with a 4-6 benzene-ethyl acetate mixture to obtain 22 g of m-(N,N-dimethylureido)-3-methoxy-crotonanilide melting at 169° C. Crystallization from acetone did not change the melting point.

Analysis: $C_{14}H_{19}N_4O_3$. Calculated: %C, 60,63; %H, 6.90; %N, 15.15. Found: %C, 60.7; %H, 7.0; %N, 15.3.

EXAMPLE 4 m-acetamido-3-methoxy-crotonanilide

STEP A: m-acetamido-acetylacetanilide 20.1 g of diketene were added to a solution of 35 g of m-aminoacetanilide in 150 ml of benzene and after stirring for an hour, the mixture was evaporated to dryness under reduced pressure. The residue was added to acetone and the mixture was filtered. The filtrate was evaporated to dryness under reduced pressure and the residue was added to ether. The mixture was vacuum filtered and the precipitate was washed and dried to obtain 50 g of m-acetamido-acetylacetanilide melting at 107° C which was used as is for the next step.

STEP B: m-acetamido-3-methoxy-crotonanilide 11.7 g of methyl orthoformate were added to a solution of 23.4 g of m-acetamido-acetylacetanilide in 250 ml of anhydrous methanol and the mixture was refluxed for 3 hours and cooled. 0.6 ml of quinoline were added thereto and the methanol was distilled off under reduced pressure. Toluene was added to the residue and the mixture was heated at 140° C for one hour while distilling a methanol-toluene azeotrope. The mixture was then concentrated to dryness under reduced pressure and the residue was chromatographed over silica gel. Elution with ethyl acetate yielded 14.5 g of m-acetamido-3-methoxy-crotonanilide melting at 167° C. Crystallization from acetone did not change the melting point.

Analysis: $C_{13}H_{16}N_2O_3$. Calculated: %C, 62.88; %H, 6.49; %N, 11.28. Found: %C, 63.1; %H, 6.6; %N, 11.3.

EXAMPLE 5 m-propionamido-3-methoxy-crotonanilide

STEP A: m-propionamido-acetylacetanilide 42 g of diketene were added to a solution of 82.1 g of m-aminopropionanilide in 400 ml of benzene and the mixture was stirred for 4½ hours and then was vacuum filtered. The recovered precipitate was washed with benzene, then isopropyl ether and dried to obtain 118 g of m-propionamido-acetylacetanilide melting at 70° C which was used as is for the next step.

STEP B: m-propionamido-3,3-dimethoxy-butyranilide 2 g of p-toluene sulfonic acid and 74 g of methyl orthoformate were added to a mixture of 111.6 g of m-propionamidoacetylacetanilide in 200 ml of methanol and the mixture was stirred for 16 hours at 20° C and then filtered. The filtrate was evaporated to dryness under reduced pressure to obtain 110 g of m-propionamido-3,3-dimethoxy-butyranilide melting at 115° C which was used as is for the next step.

STEP C: m-propionamido-3-methoxy-crotonanilide

A solution of 42.8 g of m-propionamido-3,3-dimethoxybutyranilide in 500 ml of toluene was heated at 140° C for 1 hour and was then let stand for 72 hours. The toluene was decanted and the residue was added to acetone. The mixture was filtered and the filtrate was concentrated to dryness under reduced pressure. The residue was chromatographed over silica gel and was eluted with an 8-2 methylene chloride-acetone mixture to obtain 18 g of m-propionamido-3-methoxycrotonanilide melting at 155° C. Crystallization from ethyl acetate did not change the melting point.

Analysis: $C_{14}H_{18}N_2O_3$. Calculated: %C, 64.10; %H, 6.91; %N, 10.68. Found: %C 64.3; %H, 6.8; %N, 10.5.

EXAMPLE 6 m-valeramido-3-methoxy-crotonanilide

STEP A: m-nitrovaleranilide 132.6 g of valeryl chloride were added over an hour to a mixture of 138 g of m-nitranilide, 111 g of triethylamine and 1 liter of ethyl ether cooled to 0° C and the mixture was stirred for 16 hours at 20° C and was then filtered. The filtrate was distilled to dryness under reduced pressure and the residue was taken up in chloroform. The solution was washed with water, treated with activated carbon, filtered, dried and evaporated to dryness under reduced pressure to obtain 219 g of raw m-nitrovaleranilide melting at 65° C which was used as in for the next step.

STEP B: m-aminovaleranilide

A mixture of 177.6 g of m-nitrovaleranilide, 160 ml of water, 8 ml of 22° Be hydrochloric acid and 640 ml of 95% ethanol was refluxed and 480 g of iron powder were added with stirring over 30 minutes. Reflux was continued for 30 minutes with stirring and the mixture was filtered. The filtrate was concentrated to dryness under reduced pressure and the residue was chromatographed over silica gel. Elution with an 8-2 methylene chloride-acetone mixture gave 151 g of m-aminovaleranilide with a specific rotation $n_D^{20} = 1.541$.

STEP C: m-valeramido-acetylacetanilide 42 g of diketene were added to a mixture of 96 g of m-aminovaleranilide in 400 ml of benzene and the mixture was stirred for 16 hours at 20° C. The benzene was decanted and the residue was added to refluxing benzene. The mixture was treated with activated carbon and filtered to obtain raw m-valeramido-acetylacetanilide melting at 90° C. Crystallization from ethyl acetate yielded 34 g of pure m-valeramidoacetylacetanilide melting at 116° C.

STEP D: m-valeramido-3-methoxy-crotonanilide 16.5 g of methyl orthoformate were added to a solution of 27.6 g of m-valeramido-acetylacetanilide in 50 ml of methanol and after the addition of 0.5 g of p-toluene sulfonic acid, the mixture was stirred for 72 hours at 20° C. 200 ml of toluene and 1 ml of quinoline were added and the mixture was heated at 140° C for 1 hour while distilling a methanol-toluene azeotrope. The mixture was evaporated to dryness under reduced pressure and the residue was chromatographed over silica gel. Elution with an 8-2 methylene chloride-acetone mixture yielded 20 g of m-valeramido-3-methoxy-crotonanilide melting at 115° C and after crystallization from ethyl acetate melted at 116° C.

Analysis: $C_{16}H_{22}N_2O_3$. Calculated: %C, 66.17; %H, 7.63; %N, 9.65. Found: %C, 66.2; %H, 7.6; %N, 9.4.

EXAMPLE 7 m-(3'-methoxycrotonylamino)-3-methoxy-crotonanilide

STEP A: m-(acetylacetamido)-acetylacetanilide 168 g of diketene were slowly added to a solution of 108 g of m-phenylenediamine in a liter of tetrahydrofuran and the mixture was stirred for 5 hours at 20° C and then was allowed to stand for 15 hours. The mixture was concentrated to dryness under reduced pressure and the residue was added to methanol. The mixture was vacuum filtered and the recovered precipitate was dried to obtain 180 g of m-(acetylacetamido)-acetyl acetanilide melting at 117° C. Chromatography over silica gel and elution with a 6-4 methylene chloride-acetone mixture gave a product melting at 118° C.

STEP B: m-(3'-methoxycrotonylamino)-3-methoxy-crotonanilide

A mixture of 30 g of m-(acetylacetamido)-acetylacetanilide, 30 g of methyl orthoformate, 100 ml of methanol and 1 g of p-toluene sulfonic acid was stirred at 20° C for 24 hours and after addition of 2 ml of quinoline, the mixture was distilled to dryness under reduced pressure. Toluene was added to the residue and the mixture was heated with stirring at 145° C while distilling a methanol-toluene azeotrope. The mixture was cooled and the toluene was decanted. The residue was taken up in an 8-2 methylene chloride-acetone mixture and was chromatographed over silica gel to obtain 20 g of m-(3'-methoxycrotonylamino)-3-methoxycrotonanilide melting at 196° C.

Analysis: $C_{16}H_{20}N_2O_4$. Calculated: %C, 63.14; %H, 6.62. Found: %C, 63.1; %H, 6.7.

EXAMPLE 8 m-(N-methyl-N-methoxy-ureido)-3-methoxy-crotonanilide 13.5 g of methyl methoxy carbamoyl chloride were added to a mixture of 20.6 g of m-amino-3-methoxy-crotonanilide and 11.1 g of triethylamine in 250 ml of tetrahydrofuran and the mixture was stirred at 20° C for 16 hours and was then filtered. The filtrate was evaporated to dryness under reduced pressure and the residue was taken up in isopropyl ether and dried to obtain 29 g of m-(N-methyl-N-methoxy-ureido)-3-methoxy-crotonanilide melting at 140° C. Crystallization from ethanol gave a melting point of 142° C.

Analysis: $C_{14}H_{19}N_3O_4$. Calculated: %C, 57.32; %H, 6.52; %N, 14.32. Found: %C, 57.1 %H, 6.6; %N, 14.3.

EXAMPLE 9 m-(N-methyl-ureido)-3-methoxy-crotonanilide 26 ml of methyl isocyanate were added to a mixture of 11.6 g of triethylamine and 22.3 g of m-amino-3-methoxy-crotonanilide in 250 ml of tetrahydrofuran and the mixture was stirred for 16 hours and vacuum filtered. The recovered precipitate was washed with isopropyl ether to obtain 23 g of m-(N-methyl-ureido)-3-methoxy-crotonanilide melting at 166° C. Crystallization from ethanol did not change the melting point.

Analysis: $C_{13}H_{17}N_3O_3$. Calculated: %C, 59.30; %H, 6.51; %N, 15.95. Found: %C, 59.2; %H, 6.5; %N, 15.8.

EXAMPLE 10

A wettable powder was prepared from 25% by weight of m-(n-propyloxycarbonylamino)-3-methoxy-crotonanilide, 15% by weight of Ekapersol S (condensation product of sodium naphthalene sulfonate), 0.5% by weight of Brecolane NVA (sodium alkylnaphthalene sulfonate), 34.5% by weight of Zeosil 39 (precipitated synthetic hydrated silica) and 25% by weight of Vercoryl S (colloidal Kaolin).

A second herbicidal composition was prepared consisting of 15% by weight of m-(N-methyl-ureido)-3-methoxy-crotonanilide, 6.4% by weight of Atlox 4851 (oxyethylene trigylceride with a sulfonate — Acid No. 1.5), 3.2% by weight of Atlox 4855 (oxyethylene triglyceride with a sulfonate — Acid No. 3) and 75.4% by weight of xylene.

PRE-AND POST-EMERGENCE HERBICIDAL ACTIVITY

A. m-(n-propyloxycarbonylamino)-3-methoxy-crotonanilide (compound A), m-(N,N-dimethylureido)-3-methoxy-crotonanilide (compound B), m-propionamido-3-methoxy-crotonanilide (compound C), and m-valeramido-3-methoxy-crotonanilide (compound D) were tested on plant species planted in a culture box (23 × 14 × 4 cm) with a double bottom and with watering from underneath. 20 seeds for each species were planted in rows 3 cm apart in a single box and 4 tests were run for each concentration. The plants were held at 60% relative humidity at 20° C ± 2° C with lighting by fluorescent tubes (daylight and white light) for 6 to 22 hours each day. The dirt mixture was 10 volumes of pure dirt, 2 volumes of peat and 10 volumes of river sand.

In the pre-emergence test, treatment was effected 24 hours after the sowing and the first watering was effected by aspersion so that a part of the product was carried to the level of the seeds. In the post-emergence test, treatment was effected on the above ground portion after 21 days of culture.

In both cases, the test products were applied under standard conditions with a microsprayer at doses of 5, 2.5, 1.25 and 0.625 Kg/ha at a dilution equal to 560 l/ha. The final readings was determined by the weight of the plants 21 days after the pre-emergence treatment and 15 days after the post-emergence treatment. The results in Tables I to III are expressed as a percent of reduction in vegatation P calculated as follows:

$$P = \frac{\text{weight of control plants} - \text{weight of treated plants}}{\text{weight of control plants}} \times 100$$

| COMPOUND A - POST-EMERGENCE |
| --- |

| Doses in Kg/ha | A | B | C | D | E | F | G | H | I | J | K | L | M | N |
|---|---|---|---|---|---|---|---|---|---|---|---|---|---|---|
| 5 | 40 | 31 | 70 | 39 | 100 | 100 | 100 | 100 | 100 | 100 | | 100 | 100 | 100 |
| 2.5 | 21 | 47 | 45 | 22 | 100 | 100 | 100 | 100 | 100 | 100 | | 100 | 100 | 100 |
| 1.25 | 0 | 0 | 20 | 21 | 100 | 0 | 100 | 100 | 100 | 100 | | 100 | 100 | 100 |
| 0.625 | 0 | 0 | 0 | 0 | 73 | 0 | 40 | 100 | 100 | 100 | | 100 | 100 | 100 |

| COMPOUND A - PRE-EMERGENCE |
| --- |

| Doses in Kg/ha | A | B | C | D | E | F | G | H | I | J | K | L | M | N |
|---|---|---|---|---|---|---|---|---|---|---|---|---|---|---|
| 5 | 21 | 66 | 0 | 52 | 100 | 50 | 100 | 100 | 100 | 100 | 77 | 100 | 100 | 100 |
| 2.5 | 0 | 34 | 0 | 0 | 89 | 50 | 100 | 100 | 100 | 98 | 57 | 100 | 100 | 100 |
| 1.25 | 0 | 0 | 0 | 0 | 0 | 0 | 25 | 76 | 100 | 94 | 30 | 100 | 100 | 100 |

| 0.625 | 0 | 0 | 0 | 0 | 0 | 0 | 0 | 71 | 100 | 73 | 30 | 100 | 85 | 91 |

A : Wheat
B : Barley
C : Corn
D : Oats
E : Bent grass
F : Rye-grass
G : Foxtail
H : Beets
I : Lambsquarter
J : Chrysanthemum
K : Galium
L : Mustard
M : Rumex
N : Clover

COMPOUND B - POST-EMERGENCE

| Doses in Kg/ha | A | B | C | D | E | F | G | H | I | J | K | L | M | N |
|---|---|---|---|---|---|---|---|---|---|---|---|---|---|---|
| 5 | 0 | 0 | 0 | 0 | 100 | 31 | 0 | 100 | 100 | 100 |  | 100 | 100 | 100 |
| 2.5 | 0 | 0 | 0 | 0 | 91 | 0 | 0 | 100 | 100 | 98 |  | 100 | 74 | 100 |
| 1.25 | 0 | 0 | 0 | 0 | 0 | 0 | 0 | 100 | 100 | 90 |  | 100 | 45 | 100 |
| 0.625 | 0 | 0 | 0 | 0 | 0 | 0 | 0 | 100 | 100 | 91 |  | 100 | 43 | 100 |

COMPOUND B - PRE-EMERGENCE

| Doses in Kg/ha | A | B | C | D | E | F | G | H | I | J | K | L | M | N |
|---|---|---|---|---|---|---|---|---|---|---|---|---|---|---|
| 5 | 38 | 37 | 0 | 57 | 100 | 83 | 100 | 100 | 100 | 100 | 87 | 100 | 100 | 100 |
| 2.5 | 0 | 0 | 0 | 0 | 100 | 0 | 50 | 100 | 83 | 75 | 20 | 100 | 84 | 100 |
| 1.25 | 0 | 0 | 0 | 38 | 88 | 0 | 0 | 50 | 44 | 42 | 0 | 80 | 0 | 88 |
| 0.625 | 0 | 0 | 0 | 0 | 0 | 0 | 0 | 0 | 0 | 0 | 0 | 58 | 0 | 0 |

COMPOUND C - POST-EMERGENCE

| Dose in Kg/ha | A | B | C | D | E | F | G | H | I | J | K | L | M | N |
|---|---|---|---|---|---|---|---|---|---|---|---|---|---|---|
| 5 | 0 | 0 | 0 | 0 | 80 | 19 | 26 | 100 | 100 | 100 | 100 | 100 | 100 | 100 |
| 2.5 | 0 | 0 | 0 | 0 | 71 | 0 | 38 | 100 | 100 | 100 | 100 | 100 | 100 | 100 |
| 1.25 | 0 | 0 | 0 | 0 | 0 | 0 | 0 | 100 | 100 | 100 | 100 | 100 | 100 | 100 |
| 0.625 | 0 | 0 | 0 | 0 | 0 | 0 | 0 | 0 | 100 | 97 | 100 | 100 | 98 | 71 |

COMPOUND D - POST-EMERGENCE

| Doses in Kg/ha | A | B | C | D | E | F | G | H | I | J | K | L | M | N |
|---|---|---|---|---|---|---|---|---|---|---|---|---|---|---|
| 5 | 0 | 0 | 0 | 0 | 69 | 15 | 75 | 100 | 100 | 100 | 100 | 100 | 100 | 100 |
| 2.5 | 0 | 0 | 0 | 0 | 62 | 0 | 40 | 100 | 100 | 100 | 89 | 100 | 100 | 100 |
| 1.25 | 0 | 0 | 0 | 0 | 57 | 0 | 0 | 100 | 100 | 100 | 24 | 100 | 100 | 100 |
| 0.625 | 0 | 0 | 0 | 0 | 0 | 0 | 0 | 100 | 100 | 100 | 0 | 100 | 100 | 100 |

The preceding tests show that the compounds possess an excellent pre- and post-emergence herbicidal activity and show a good selectivity against a number of plants, particularly in regard to the cereals, beets and corn making them useful as selective herbicides for these crops.

The herbicidal activity of m-(N-methyl-N-methoxy-ureido)-3-methoxy-crotonanilide (compound E) and m-(N-methyl-ureido)-3-methoxy-crotonanilide (compound F) was determined in the same fashion. The final readings were determined by counting the plants 21 days after pre-emergence treatment and 15 days after post-emergence treatment. The results were expressed as percent of mortality M:

$$M = \frac{\text{No. of control plants} - \text{No. of treated living plants}}{\text{No. of control plants}} \times 100$$

COMPOUND E - POST-EMERGENCE

| Treated Plants | Doses in Kg/ha | | | |
|---|---|---|---|---|
|  | 5 | 2.5 | 1.25 | 0.625 |
| Triticum Sativum | 100 | 63 | 0 | 0 |
| Hordeum Spec. | 100 | 68 | 0 | 0 |
| Zea Mays | 24 | 0 | 0 | 0 |
| Avena Sativa | 100 | 19 | 0 | 0 |
| Agrostis Tenuis | 100 | 100 | 100 | 0 |
| Lolium Perenne | 100 | 41 | 0 | 0 |
| Alopecurus Myosuroides | 100 | 100 | 21 | 22 |
| Beta Vulgaris | 100 | 100 | 100 | 100 |
| Chenopodium Quinoa | 100 | 100 | 100 | 100 |
| Chrysanthemum Coronarium | 100 | 100 | 100 | 100 |
| Galium Aparine | 100 | 100 | 100 | 54 |
| Sinapis Alba | 100 | 100 | 100 | 100 |
| Rumex Crispus | 100 | 100 | 100 | 100 |
| Trifolium Praetense | 100 | 100 | 100 | 100 |

COMPOUND E - PRE-EMERGENCE

| Treated Plants | Doses in Kg/ha | | | |
|---|---|---|---|---|
|  | 5 | 2.5Z | 1.25 | 0.625 |
| Triticum Sativum | 55 | 55 | 0 | 0 |
| Hordeum Spec | 69 | 31 | 0 | 0 |

| COMPOUND E - PRE-EMERGENCE | | | | |
|---|---|---|---|---|
| Treated | Doses in Kg/ha | | | |
| Plants | 5 | 2.5Z | 1.25 | 0.625 |
| Zea Mays | 0 | 0 | 0 | 0 |
| Avena Sativa | 100 | 100 | 0 | 0 |
| Agrostis Tenuis | 100 | 100 | 100 | 93 |
| Lolium Perenne | 100 | 100 | 39 | 0 |
| Alopecurus Myosuroides | 52 | 69 | 0 | 0 |
| Beta Vulgaris | 100 | 100 | 100 | 100 |
| Chenopodium Quinoa | 100 | 100 | 100 | 100 |
| Chrysanthemum Coronarium | 100 | 100 | 100 | 100 |
| Galium Aparine | 82 | 91 | 78 | 60 |
| Spinapis Alba | 100 | 100 | 100 | 100 |
| Rumex Crispus | 100 | 100 | 100 | 100 |
| Trifolium Praetense | 100 | 100 | 100 | 100 |

| COMPOUND F - POST-EMERGENCE | | | | |
|---|---|---|---|---|
| Treated | Doses in Kg/ha | | | |
| Plants | 5 | 2.5 | 1.25 | 0.625 |
| Triticum Sativum | 0 | 0 | 0 | 0 |
| Hordeum Spec | 0 | 0 | 0 | 0 |
| Zea Mays | 0 | 0 | 0 | 0 |
| Avena Sativa | 0 | 0 | 0 | 0 |
| Agrostis Ienuis | 100 | 89 | 73 | 0 |
| Lolium Perenne | 0 | 0 | 0 | 0 |
| Alopecurus Myosuroides | 37 | 0 | 0 | 0 |
| Beta Vulgaris | 100 | 100 | 100 | 100 |
| Chenopodium Quinoas | 100 | 100 | 100 | 100 |
| Chrysanthemum Coronarium | 100 | 100 | 100 | 95 |
| Galium Aparine | 100 | 55 | 0 | 0 |
| Sinapis Alba | 100 | 100 | 100 | 100 |
| Rumex Crispus | 100 | 100 | 71 | 33 |
| Trifolium Praetense | 100 | 100 | 100 | 71 |

| COMPOUND F - PRE-EMERGENCE | | | | |
|---|---|---|---|---|
| Treated | Doses in Kg/ha | | | |
| Plants | 5 | 2.5 | 1.25 | 0.625 |
| Triticum Sativum | 0 | 0 | 0 | 0 |
| Hordeum Spec. | 0 | 0 | 0 | 0 |
| Zea Mays | 0 | 0 | 0 | 0 |
| Avena Sativa | 0 | 0 | 0 | 0 |
| Agrostis Tenuis | 100 | 100 | 93 | 54 |
| Lolium Perenne | 50 | 23 | 0 | 0 |
| Alopecurus Myosuroides | 38 | 40 | 33 | 44 |
| Beta Vulgaris | 100 | 46 | 42 | 0 |
| Chenopodium Quinoa | 100 | 47 | 41 | 43 |
| Chrysanthemum Coronarium | 100 | 75 | 0 | 0 |
| Galium Aparine | 76 | 0 | 0 | 0 |
| Sinapis Alba | 100 | 100 | 91 | 0 |
| Rumex Crispus | 100 | 0 | 0 | 0 |
| Trifolium Praetense | 100 | 60 | 0 | 0 |

The test data in the Tables show that compounds E and F destroyed the weeds at practical dosages for herbicidal use without attacking the grass crops.

Various modifications of the products and methods of the invention may be made without departing from the spirit or scope thereof and it should be understood that the invention is to be limited only as defined in the appended claims.

We claim:

1. A compound of the formula

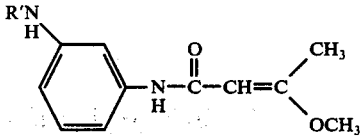

wherein R' is selected from the group consisting of

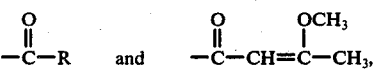

R is alkyl of 1 to 6 carbon atoms.

2. A compound of claim 1 wherein R' is

3. A compound of claim 1 which is m-acetamido-3-methoxy-crotonanilide.

4. A compound of claim 1 which is m-propionamido-3-methoxy-crotonanilide.

5. A compound of claim 1 which is m-valeramido-3-methoxy-crotonanilide.

6. A compound of claim 1 which is m-(3'-methoxy-crotonylamino)-3-methoxy-crotonanilide.

7. An herbicidal composition comprising a herbicidally effective amount of a compound of claim 1 and an inert carrier.

8. A method of killing weeds comprising contacting weeds with a herbicidally effective amount of a compound of claim 1.

9. The method of claim 8 wherein the compound is applied pre-emergence.

10. The method of claim 8 wherein the compound is applied post-emergence.

11. The method of claim 8 wherein R' is

* * * * *